United States Patent [19]

Schwemmer

[11] 4,229,839
[45] Oct. 28, 1980

[54] JOINT PROSTHESIS

[75] Inventor: Leonard J. Schwemmer, Erie, Pa.

[73] Assignee: Lord Corporation, Erie, Pa.

[21] Appl. No.: 852,183

[22] Filed: Nov. 16, 1977

[51] Int. Cl.³ .......................... A61F 1/03; A61F 1/04; A61F 1/08

[52] U.S. Cl. .......................................... 3/1.91; 3/32; 403/120; 403/224

[58] Field of Search ................... 3/1.91, 1.911, 1.912, 3/1.913, 17 R, 18, 22, 29, 30, 31, 32, 12, 12.2, 12.4; 403/224, 120, 225, 228

[56] References Cited

U.S. PATENT DOCUMENTS

| | | | |
|---|---|---|---|
| 1,911,440 | 5/1933 | Desoutter | 3/31 |
| 2,183,076 | 12/1939 | Kaiser | 3/6 |
| 2,605,475 | 8/1952 | Burger et al. | 3/32 |
| 2,692,392 | 10/1954 | Bennington et al. | 3/33 |
| 2,819,105 | 1/1958 | Behnke | 403/224 |
| 3,147,963 | 9/1964 | Frazier | 403/224 X |
| 3,147,964 | 9/1964 | Wolf | 403/224 X |
| 3,467,421 | 9/1969 | Bentley | 403/203 |
| 3,480,972 | 12/1969 | Prahl | 3/33 |
| 3,875,594 | 4/1975 | Swanson | 3/1 |
| 3,916,451 | 11/1975 | Buechel et al. | 3/1.91 |
| 3,982,280 | 9/1976 | Asbelle et al. | 3/32 |
| 4,038,705 | 8/1977 | Owens et al. | 3/2 |
| 4,068,868 | 1/1978 | Ohrt | 285/263 |

FOREIGN PATENT DOCUMENTS 72709 9/1946 Norway .................................. 3/31

*Primary Examiner*—Clifford D. Crowder
*Attorney, Agent, or Firm*—Maurice R. Salada; James W. Wright

[57] ABSTRACT

A joint prosthesis comprises two relatively inextensible primary components that are spaced apart from one another. Disposed between and spaced from both of the components is a pivot member. The pivot member is resiliently secured to each of the primary components so as to permit relative rotation between the primary components and the pivot member. As a result, the two primary components of the prosthesis can rotate toward and away from each other about an axis that is disposed at least adjacent to and at least approximately parallel to a central longitudinal axis of the pivot member. The pivot member and the primary components of the prosthesis are preferably secured together by one or more bodies of elastomer.

39 Claims, 9 Drawing Figures

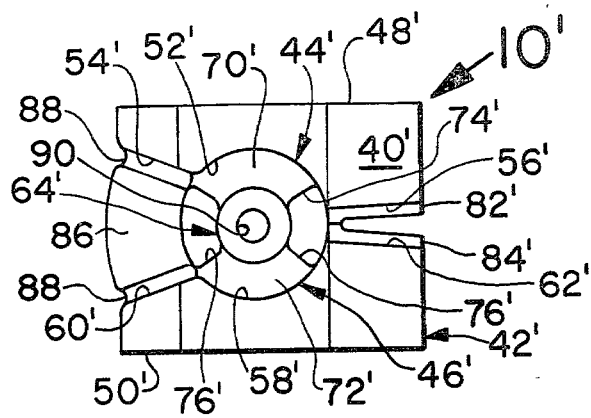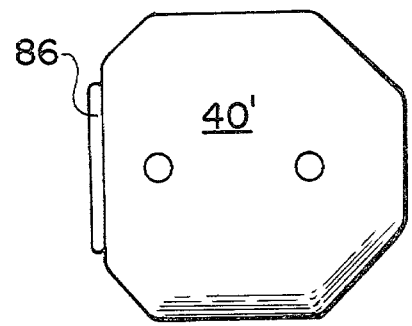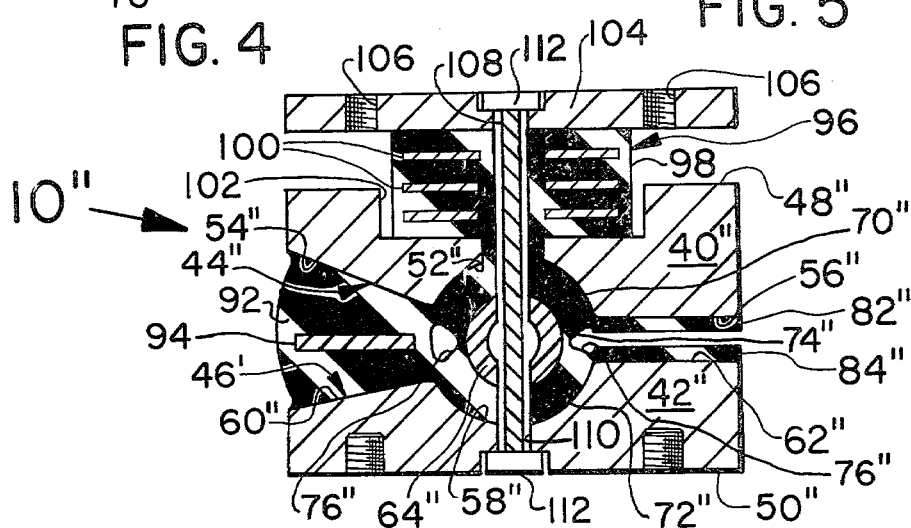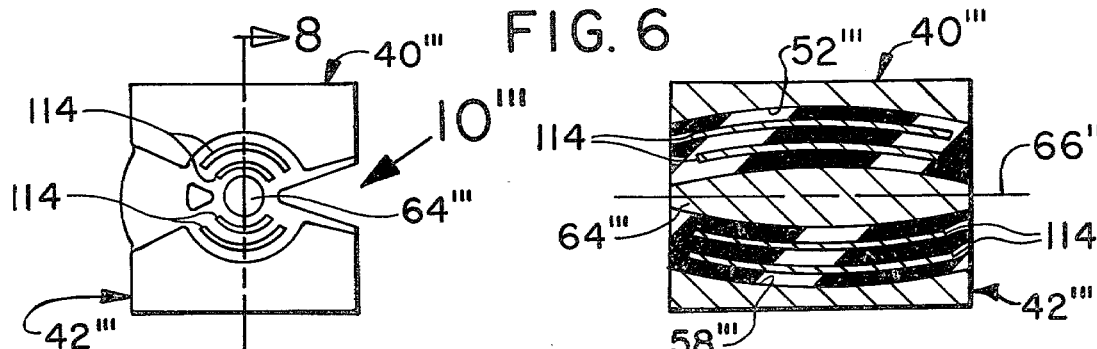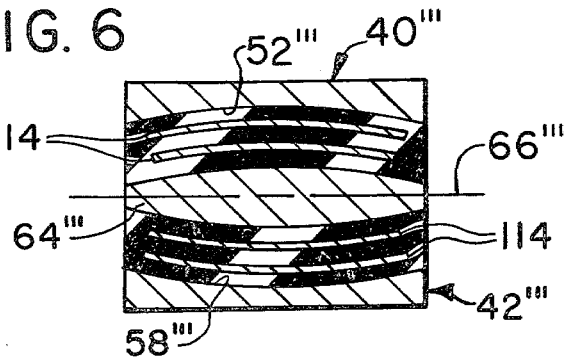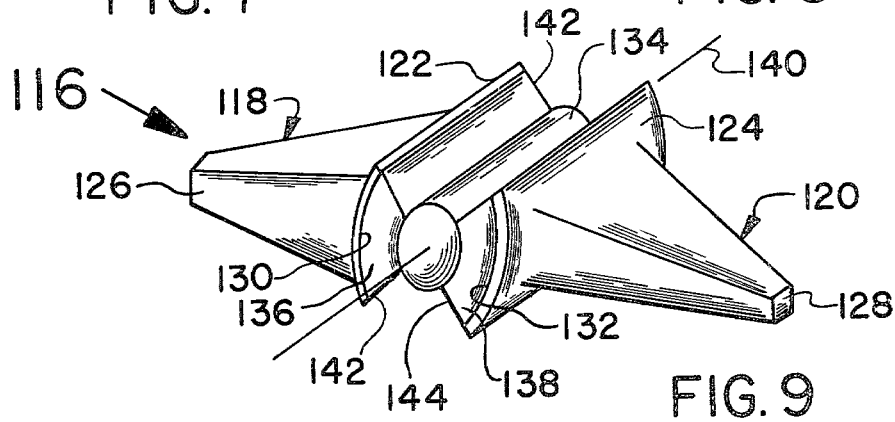

JOINT PROSTHESIS

RELATED APPLICATIONS

The present application describes, illustrates, and claims joint prostheses that are similar in structure and operation to joint prostheses described, illustrated, and claimed in two commonly owned, concurrently filed applications of James B. Koeneman, entitled "Knee Joint Prosthesis" (Ser. No. 852,111) and "Joint Prosthesis With Contoured Pin" (Ser. No. 852,181), and in a commonly owned, concurrently filed joint application (Ser. No. 852,182) of Leonard J. Schwemmer and Howard T. Wilson, entitled "Ankle Joint Prosthesis".

BACKGROUND OF THE INVENTION

Resilient materials, such as elastomers, have long been used in external prosthetic devices for the human body to cushion impact or shock loads. Because impact loads are necessarily and regularly encountered in walking, two common prosthetic devices that have often incorporated resilient materials are artificial feet and ankle joint prostheses for use with artificial feet. In early designs, an ankle joint prosthesis was typically a metallic pivot that included a plain (e.g., sleeve) bearing or a rolling element (e.g., ball) bearing. Resilient or elastomeric material was disposed both about the pivot to help limit its motion and in various portions of an associated artificial foot to cushion or absorb impact loads. Typical combinations of a cushioned artificial foot and an ankle joint prosthesis that incorporates a metal-on-metal pivot are described and illustrated in Ehle U.S. Pat. No. 487,697, Rowley U.S. Pat. No. 1,090,881, and Kaiser U.S. Pat. No. 2,183,076.

Later in the development of ankle joint prostheses for external use, resilient or elastomeric material came to be utilized for properties other than its ability to absorb or cushion impact loads. In Desoutter U.S. Pat. No. 1,911,440, for example, a tubular rubber bushing is secured between a pin and a metal sleeve that circumscribes the pin to form a pivot for an ankle joint prosthesis. The outer sleeve is connected to an artificial foot, while the pin is connected to an artificial lower leg. Articulation is permitted by torsional deflection of the bushing. Because of the resilience of the bushing material, the ankle joint prosthesis automatically returns to a preselected position after it is deflected. The prosthesis also does not require lubrication because the bushing separates the adjacent metal surfaces of the pin and the sleeve. Similar ankle joint prostheses that employ a tubular bushing or body of elastomer between an outer rigid sleeve and an inner pin or sleeve are described and illustrated in Burger et al U.S. Pat. No. 2,605,475 and Prahl U.S. Pat. No. 3,480,972.

A pivot or pivotable assembly that incorporates a relatively thin, tubular body of elastomer secured between a pin and a larger diameter sleeve is only capable of extensive pivotal or rotational movement about a single axis. In a typical ankle joint prosthesis, such as the Desoutter and Prahl prostheses, such an elastomeric pivot is oriented generally perpendicular to the longitudinal axis of the wearer's leg and transverse to the longitudinal axis of the wearer's artificial foot. In the orientation that has been described, the elastomeric pivot permits extensive flexion in the dorsal and plantar directions. An elastomeric pivot so oriented, however, can only provide a limited degree of inversion and eversion of a foot about its longitudinal axis or a parallel axis and only a limited degree of internal and external rotation of the foot about the longitudinal axis of the leg. The motions other than flexion are all accommodated primarily through compression of the elastomeric bushing, which is relatively thin and cannot afford any significant degree of deflection. To overcome some of the motion limitations inherent in the ankle joint prostheses of the Desoutter and Prahl patents, the ankle joint prosthesis of the previously mentioned Burger et al patent incorporates two elastomeric pivots disposed at right angles to each other. The Burger et al ankle joint prosthesis thus can resiliently permit both extensive dorsal and plantar flexion and extensive inversion and eversion. Other external ankle joint prostheses attempt to provide the three types of movement afforded by a natural ankle joint through the use of relatively massive blocks of elastomer, rather than the tubular bushings discussed above. The blocks of elastomer may be specially shaped or contoured in order to provide appropriate stiffnesses or motion capabilities in the three critical rotational directions. Examples of external ankle joint prostheses that incorporate large blocks of elastomer are described and illustrated in Bennington et al U.S. Pat. No. 2,692,392 and Asbelle et al U.S. Pat. No. 3,982,280.

Although resilient materials, and particularly elastomeric materials, have for many years been suggested for use in external joint prostheses, the use of resilient or elastomeric materials in internal joint prostheses has only recently been proposed. The apparent delay in the appearance of proposals for the use of resilient or elastomeric materials internally of the human body is probably attributable in part to the lack of a physiologically inert elastomeric material that could safely be used in the body. Nonetheless, with the development of suitable elastomeric materials, such as Dow Corning Corporation's Silastic ® silicone elastomer, a number of surgically implantable, elastomeric joint prostheses have been proposed, particularly for finger joints. The finger joint prostheses, in particular, tend to be entirely formed of elastomer or nearly so. Unfortunately, such designs require the elastomer to be bent or flexed extensively at some point to provide a pivot. The result is alternating tension and compression loading of the elastomer, which is detrimental to its long-term fatigue life. The use of notches in the elastomer to locate the pivot point further adds to the stresses in the elastomer. Examples of finger joint prostheses that are entirely formed of elastomer or nearly so are described and illustrated in Swanson U.S. Pat. No. 3,462,765, Niebauer et al U.S. Pat. No. 3,593,342, Lynch U.S. Pat. No. 3,681,786, and Swanson U.S. Pat. No. 3,875,594. Other than the finger joint prostheses mentioned above, relatively few implantable prostheses that employ resilient or elastomeric material have been identified. Nonetheless, the use of elastomeric material in an implantable hip joint prosthesis is suggested in Buechel et al U.S. Pat. No. 3,916,451, particularly FIG. 1, and in Bokros et al U.S. Pat. No. 3,707,006, particularly FIG. 5.

The ankle joint prostheses described in the previously mentioned patents to Desoutter, Burger et al, and Prahl appear to represent the best presently known designs for use of the desirable properties of elastomeric material in a prosthesis that accommodates pivotal or rotational motion. Nonetheless, the elastomeric pivots that are incorporated in the ankle joint prostheses of these three patents do not make optimal use of elastomeric material within the space provided. In particular, the relatively thin, tubular bodies of elastomer in the ankle joint prostheses of Desoutter, Burger et al, and Prahl are subjected to relatively high, torsionally-induced strains which, over periods of extended use, will lead to failure of the elastomeric bodies. While the strains experienced by the elastomeric bodies of the patented ankle joint prostheses may not be detrimental in terms of a few hundred or even a few thousand articulations of the prostheses, the strains are critical when one considers several million articulations or deflections of the prostheses. Such numbers of articulations may easily be experienced during a year or two of normal use. In an ankle joint prosthesis that is used externally of the human body, replacement of the elastomeric elements of the prosthesis may merely represent additional expense and some inconvenience to the user. If such a joint prosthesis were implanted in the body of the user, on the other hand, failure of the elastomeric elements within one or two years would seriously limit the desirability of using such a prosthesis.

SUMMARY OF THE INVENTION

The present invention is directed to a joint prosthesis which is suitable for either internal or external use and which is constructed resiliently to permit and accommodate pivotal or rotational movement, with a view to providing maximum useful life. A joint prosthesis according to the invention comprises a pair of primary components that are formed of relatively inextensible material and are spaced apart from one another. Disposed between and spaced from each of the two components is a pivot member that is also formed of relatively inextensible material. The pivot member is resiliently secured to each of the primary components so as to permit and accommodate relative rotation between the pivot member and the components. As a result, the two primary components of the prosthesis can rotate toward and away from each other about an axis that is disposed at least adjacent to and at least approximately parallel to a central axis of the pivot member. The use of a pivot member and a pivot axis that are separate from the primary components of a joint prosthesis permits the prosthesis to have, for example, a relatively small size for a given angular motion to be accommodated and a given maximum strain in the material that resiliently secures the pivot member to the primary components. Alternatively, the prosthesis of the present invention will permit, for a given angular motion to be accommodated and a given size of the prosthesis, a lower maximum strain in and a larger service life for the resilient material that secures together the pivot member and the primary components of the prosthesis. The foregoing advantages are experienced particularly with reference to a prosthesis such as the prostheses of Desoutter U.S. Pat. No. 1,911,440 and Prahl U.S. Pat. No. 3,480,972, in which the pivot member or pin is rigidly secured to one of the primary components of the prosthesis.

In a preferred embodiment of the invention, the pivot member is secured to the primary components of the prosthesis by a member that is at least partially formed of elastomer. Attachment of the pivot member to the primary components only through a member or body that is resilient in whole or part will insure that the prosthesis is free of any relatively inextensible, and hence motion restraining, connection between the primary components. The resilient securing member will typically include a first portion that secures the pivot member to one of the primary components of the prosthesis and a second portion that secures the pivot member to the other primary component of the prosthesis. The two portions of the resilient securing member are preferably arcuately shaped when viewed in section taken generally normal to the central longitudinal axis of the pivot member. Each of the first and second portions of the securing member will also preferably include a pair of exposed surfaces that extend generally lengthwise of the pivot member and outwardly from adjacent the pivot member. The exposed surfaces of one portion of the resilient securing member are spaced apart from the exposed surfaces of the other portion of the securing member throughout at least a majority of their respective lengths measured generally radially of the pivot member. Such a spacing between the two portions of the resilient securing member facilitates relative pivotal motion or rotation between the pivot member and either of the primary components of the prosthesis without interference from the other primary component of the prosthesis or its associated portion of the securing member. Also to facilitate relative pivotal motion or rotation, each of the primary components of the prosthesis will preferably include a surface that is concavely arcuate in shape when viewed in section taken generally normal to the central longitudinal axis of the pivot member. Each of the arcuate surfaces of the primary components is presented to and spaced from a convexly arcuate surface of the pivot member. At least one of the two primary components of the prosthesis should include structure for attaching the component to a limb associated with the human body.

When the present invention is embodied in an external ankle joint prosthesis, for example, the securing member that includes two portions which resiliently secure the primary components of the prosthesis to the pivot member also includes a portion secured to at least one of the primary components at a point behind an arcuate surface of the component which is presented to the pivot member. This third portion of the securing member extends from the primary component to which it is attached toward the other primary component of the prosthesis resiliently to limit relative rotation between the two primary components, particularly relative rotation between the rear portions of the primary components. The resilient securing member may also include a fourth portion that is secured to at least one of the two primary components of the prosthesis at a point in front of the arcuate surface of the component which is presented to the pivot member. The fourth portion of the securing member extends from the component to which it is secured toward the other primary component of the prosthesis. With such an orientation, the fourth portion of the securing member resiliently limits relative rotation between the front of one primary component and the front of the other primary component. Each of the third and fourth portions of the securing member should be at least partially formed of elastomer. The opposed surfaces of the two primary components of the ankle joint prosthesis should each include an arcuately shaped portion presented to the pivot member of the prosthesis, a portion disposed in front of the arcuate portion, and a portion disposed to the rear of the arcuate portion. The front portions of the opposed surfaces of the two primary components should be disposed to diverge from one another in a direction away from the pivot member. The rear portions of the two opposed surfaces should be similarly disposed.

BRIEF DESCRIPTION OF THE DRAWINGS

For a better understanding of the invention, reference may be made to the following description of several exemplary embodiments, taken in conjunction with the figures of the accompanying drawings, in which:

FIG. 4 is a side view of a second ankle joint prosthesis according to the invention;

FIG. 5 is a plan view of the joint prosthesis of FIG. 4;

FIG. 6 is a side view, in section, of another embodiment of an ankle joint prosthesis according to the invention;

FIG. 7 is a side view of yet another embodiment of an ankle joint prosthesis according to the invention;

FIG. 8 is a sectional view of the ankle joint of FIG. 7, taken along line 8—8 of FIG. 7; and FIG. 9 is a perspective view of an endoprosthetic finger joint according to the invention.

DESCRIPTION OF EMBODIMENTS

Figure 1:
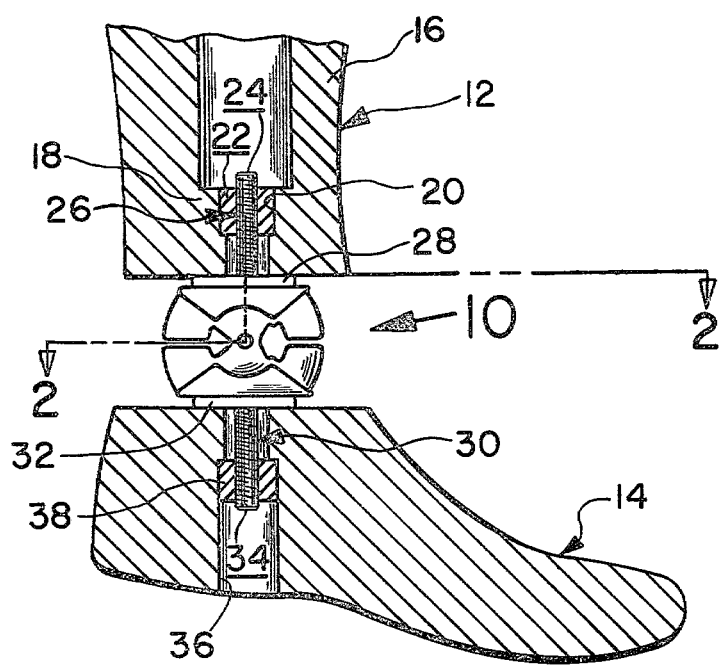
FIG. 1 is a side view of an ankle joint prosthesis according to the invention mounted between an artificial leg and an artificial foot.
Figure 2:
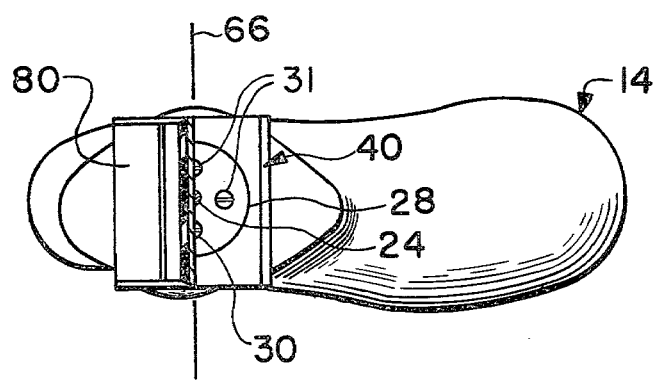
FIG. 2 is a plan view, partly in section, of the joint prosthesis of FIG. 1, taken along line 2—2 of FIG. 1.

FIG. 1 of the drawings illustrates, in side view, an ankle joint prosthesis 10, according to the present invention, mounted between an artificial lower leg 12 and an artificial foot 14. The artificial leg 12 may be formed of any one of a number of materials that have the strength necessary to support the weight of the human body, such as metal, wood, nylon, or reinforced plastic. The leg 12 is hollow and includes a generally tubular body portion 16 and an end wall 18 that is disposed adjacent the prosthesis 10. The end wall 18 is formed with an opening 20 which extends axially of the leg 12 and which receives and fixedly mounts a nut 22. Screwed into the nut 22 is the threaded stud 24 of a metal mounting adapter 26. The adapter 26 includes both the threaded stud 24 and a circular base plate 28 from one side of which the stud projects in a direction perpendicular to the plane of the base plate. As best shown in FIG. 2, the base plate 28 has four circumferentially spaced apart holes formed in it. Each of the holes in the base plate 28 receives a screw 31 that is screwed into an upper surface of the ankle joint prosthesis 10 to secure the mounting adapter 26 to the prosthesis. A second metal mounting adapter 30, which is, but need not be, identical to the adapter 26, is secured to a lower surface of the prosthesis 10 opposite the surface to which the adapter 26 is secured. Four screws (not shown) are received in holes formed in the base plate 32 of the adapter 30 and are screwed into the prosthesis 10. A threaded stud 34, which is immovably connected to the base plate 32, extends perpendicularly away from the plane of the base plate and into an opening 36 formed vertically through the artificial foot 14 just forward of the heel of the foot. The opening 36 in the foot 14 receives and fixedly mounts a nut 38 into which the threaded stud 34 is screwed. The artificial foot 14, like the artificial leg 12, is formed of a material, such as metal, wood, nylon, or reinforced plastic, that is strong enough to support the weight of the human body. In addition, the material of which the foot 14 is formed should also afford some resilience or give. Resilence of the foot will attenuate, to some extent, the shock loads imposed on the foot and transmitted from the foot through the ankle joint prosthesis 10 and the artificial leg 12 to the user's body when the foot strikes a hard surface, as in walking. Additional resilience may be provided by incorporating within the artificial foot 14 one or more bodies of elastomer or other resilient material. A typical artificial foot that incorporates several discrete bodies of elastomer disposed to provide additional resilience is described and illustrated in Kaiser U.S. Pat. No. 2,183,076.

The ankle joint prosthesis 10 incorporates two identical and vertically spaced apart primary components 40 and 42. Each of the primary components 40 and 42 is formed of a relatively inextensible material, such as metal, plastic, or reinforced plastic. The material of which the primary components 40 and 42 are formed must be suitable for bonding to elastomer, for reasons that will become apparent, and is to be judged as to its relative inextensibility through comparison to the elastomer utilized in the prosthesis 10. The components 40 and 42 incorporate contoured surfaces 44 and 46, respectively, which are presented toward, but spaced apart from each other. Opposite their respective contoured surfaces 44 and 46, the components 40 and 42 have generally planar surfaces 48 and 50, respectively. The planar surface 48 of the component 40 is presented to and juxtaposed with the surface of the adapter base plate 28 opposite the stud 24. The screws 30 that are received in the holes in the base plate 28 are screwed into threaded, blind bores (not shown) formed in the surface 48 and the component 40. In a similar manner, the planar surface 50 of the component 42 is presented to and juxtaposed with the surface of the adapter base plate 32 opposite the stud 34. The screws (not shown) that are received in the holes (not shown) in the base plate 32 are screwed into threaded, blind bores (not shown) formed in the planar surface 50 and the component 42. Although the primary components 40 and 42 of the prosthesis 10 are attached to separate mounting adapters 26 and 32, respectively, the studs 24 and 34 of the adapters could each be formed in one piece with an adjacent primary component.

The contoured surface 44 of the primary component 40 of the prosthesis 10 includes a central portion 52 that is concavely arcuate in shape, when viewed from the side, as in FIG. 1. To the rear of its central portion 52, the surface 44 includes a planar rear portion 54 that slopes toward the surface 48 from front to rear of the prosthesis 10. In front of its central portion 52, the surface 44 includes a planar front portion 56 that slopes toward the surface 48 from rear to front of the prosthesis 10. The contoured surface 46 of the component 42 similarly includes a concavely arcuate central portion 58, a planar rear portion 60, and a planar front portion 62. The front and rear portions 62 and 60 of the surface 48 slope toward the surface 50. Disposed between the spaced apart arcuate portions 52 and 58 of the contoured surfaces 44 and 46 is a cylindrical pivot member or pin 64. The pin 64 is formed of a relatively inextensible material, such as metal, reinforced plastic, or nylon, and is oriented such that its central longitudinal axis 66 is generally perpendicular to the longitudinal axis of the leg 12 and transversely disposed relative to the longitudinal axis of the foot 14. Because of its shape and orientation, the pin 64 presents a convexly arcuate surface to each of the arcuate surface portions 52 and 58 of the primary components 40 and 42, respectively, of the prosthesis 10. The pin 64 is resiliently secured to the components 40 and 42 of the prosthesis 10 by a body or mass of resilient material 68, such as elastomer. The elastomer in the mass 68 may be natural rubber or a synthetic elastomer. Although all of the resilient material in the prosthesis 10 is part of a single interconnected mass 68, each of the various portions or sections of the mass 68 which are described hereinafter may be formed as a discrete member if such a procedure appears desirable for manufacturing or other purposes.

The convexly arcuate, outer circumferential surface of the pin 64 is resiliently secured to the arcuate surface portion 52 of the component 40 by an arcuately shaped portion 70 of the resilient or elastomeric mass 68. When viewed in section taken normal to the longitudinal axis 66 of the pin 64, the elastomeric portion or section 70 resembles a truncated wedge taken from an annulus. The elastomeric section 70 is bonded, by vulcanization or adhesives, for example, to both a portion of the convexly arcuate outer surface of the pin 64 and to the generally parallel portion 52 of the surface 44. To secure the pin 64 to the other primary component 42, a similar arcuately shaped portion or section 72 of the mass of elastomer 68 is disposed between and bonded to a portion of the convexly arcuate outer surface of the pin 52 and to the concavely arcuate surface portion 58 of the component 42. The elastomeric sections 70 and 72 include pairs of exposed surfaces 74 and 76, respectively, that extend lengthwise of the pin 64 and outwardly, in a generally radial direction, from the outer circumferential surface of the pin. Throughout most of their lengths, as measured radially of the pin 64, the exposed surfaces 74 of the elastomeric section 70 are spaced apart from the exposed surfaces 76 of the elastomeric section 72. The surfaces 74 do intersect the surfaces 76 adjacent the pin 64, but diverge from the surfaces 76 with increasing radial distance from the pin. In a similar manner, the front planar portion 56 of the contoured surface 44 of the component 40 diverges from the front planar portion 62 of the contoured surface 46 of the component 42. The rear portions 54 and 60 of the surfaces 44 and 46 also diverge with increasing radial distance from the pin 64. As a result of the divergence between the surfaces 74 and 76 and between the surface portions 56 and 62 and 54 and 60, there can be relative pivotal or rotational movement between the pin 64 and the primary component 40, for example, without interference between the elastomeric section 70 that will be deflected to accommodate such relative rotation and the elastomeric section 72 and without interference between the two primary components 40 and 42 of the prosthesis 10.

The elastomeric portions 70 and 72 of the mass of elastomer 68 in the prosthesis 10 will resiliently permit and, to a limited extent, resiliently resist relative rotation between the pin 64, on the one hand, and the primary components 40 and 42, on the other hand. Rotational or pivotal motion that corresponds to dorsal or plantar flexion of a natural ankle joint will occur about an axis that is disposed at least adjacent to and at least approximately parallel to the longitudinal axis 66 of the pin 64. Although the elastomeric sections 70 and 72 will offer some resilient resistance to dorsal and plantar flexion, the elastomer will be loaded in torsional shear and will not offer sufficient resistance to flexion to cushion and limit this motion. Thus, secured to the rear portions 54 and 60 of the contoured surfaces 44 and 46 of the components 40 and 42 are rear elastomeric bumper portions 78 and 80, respectively, of the elastomeric mass 68. Each of the rear bumpers 78 and 80 extends away from the surface portion 54 or 60 to which the bumper is secured and toward the other rear bumper. Nonetheless, the rear bumpers 78 and 80 are separate from each other and are spaced slightly apart when the prosthesis 10 is in its normal undeflected position. Consequently, no tension load will be applied to either of the bumpers 78 and 80, when, for example, relative rotation between the primary components 40 and 42 of the prosthesis 10 causes the rear portions 54 and 60 of the surfaces 44 and 46 to move away from each other. The ankle joint prosthesis 10 also includes front bumpers 82 and 84 that are portions of the mass of elastomer 68 incorporated in the prosthesis. The front bumpers 82 and 84 are secured to front portions 56 and 62, respectively, of the contoured surfaces 44 and 46 of the primary components 40 and 42. Each of the bumpers 82 and 84 extends away from the surface 44 or 46 to which it is secured and toward the other front bumper. Like the rear bumpers 78 and 80, the bumpers 82 and 84 are not joined together so that no tension loads can be imposed on the bumpers 82 and 84, when, for example, relative rotation between the components 40 and 42 of the prosthesis 10 causes the surface portions 56 and 62 to move away from each other. As should be apparent, the bumpers 78, 80, 82, and 84 will resist flexion of the prosthesis 10 through compression loading of the elastomer in the bumpers.

The operation of the ankle joint prosthesis 10 will be described with the user or wearer extending the artificial leg 12 and foot 14 to take a step. As the heel of the artificial foot 14 strikes the ground, the rear of the primary component 40 of the prosthesis 10 rotates toward the rear of the primary component 42 about the axis 66 of the pin 64. The elastomeric portions 70 and 72 that secure the components 40 and 42 to the pin 64 deflect in torsional shear to permit the relative rotation that occurs between the primary components and the pin. At the same time, the rear bumpers 78 and 80 come together and are compressed to limit the rotational movement and to help absorb the impact load imposed on the foot 14. As the weight of the user or wearer of the prosthesis 10 comes forward on the prosthesis and the foot 14, the rear of the component 40 begins to rotate away from the rear of the component 42. The rotation relieves the torsional deflection of the elastomeric portions 70 and 72 and the compression loads on the bumpers 78 and 80. As the weight of the user and the leg 12 continue to move forward, the elastomeric portions 70 and 72 are again deflected in torsional shear and the front bumpers 82 and 84 come together and are compressed so as to limit relative movement of the front of the component 40 toward the front of the component 42. When the user lifts the artificial foot 14 from the ground, as he prepares to take another step, the loads on the bumpers 82 and 84 and the elastomeric portions 70 and 72 are relieved.

The primary motion that the prosthesis 10 is designed to accommodate is dorsal and plantar flexion of the foot 14 with respect to the artificial leg 12. Flexion occurs about an axis disposed generally perpendicular to the longitudinal axis of the leg 12 and transverse to the longitudinal axis of the foot 14 or, in other words, about an axis that is at least adjacent to and at least approximately parallel to, if not coincident with, the longitudinal axis 66 of the pin 64. Coincidence between the axis of rotation and the axis 66 will depend, in part, on whether the pin 64 shifts during rotation between it and a primary component 40 or 42. Incorporation or resilient material into the prosthesis 10 also permits the prosthesis to accommodate limited degrees of internal and external rotation, as well as inversion and eversion, of the artificial foot 14. To permit inversion and eversion of the foot 14, which is rotation about an axis generally parallel to the longitudinal axis of the foot, the primary components 40 and 42 of the prosthesis 10 must rotate toward each other adjacent one or the other of the two sides of the prosthesis. The relative rotation between the components 40 and 42 is accommodated by compression of the two elastomeric portions 70 and 72 adjacent one side of the prosthesis 10 or one end of the pin 64. Adjacent the other side of the prosthesis 10 and the other end of the pin 64, the elastomeric portions 70 and 72 may be placed in tension as the primary components 40 and 42 rotate away from each other. Alternatively, the weight of the user or wearer of the prosthesis 10 may impose a sufficient compressive preload on the elastomeric portions 70 and 72 so that the relative rotation of the components 40 and 42 away from each other merely relieves the preload without imposing tension loads.

External and internal rotation of the foot 14, which occurs about an axis that is generally parallel to, if not coincident with, the longitudinal axis of the leg 12, is accommodated primarily through shearing deflection of the elastomeric portions 70 and 72. Because of the spaces between the exposed surfaces 74 and 76 of the elastomeric portions 70 and 72, respectively, and because of the spacing between the primary components 40 and 42, there is essentially no compression of elastomer required to accommodate rotation of the foot 14. Consequently, external and internal rotation is accomplished more easily or with less force than inversion or eversion. If the prosthesis 10 is unable to provide a sufficient degree of rotation, a supplemental rotator may be used with the prosthesis. Such a rotator would be disposed between the upper primary component 40 of the prosthesis 10 and the artificial lower leg 12, for example. Typical supplemental rotators are described and illustrated in Moore U.S. Pat. No. 3,956,775, Haupt U.S. Pat. No. 4,007,497, and Owens et al U.S. Pat. No. 4,038,705.

Although the ankle joint prosthesis 10 of FIGS. 1 and 2 may be perceived as having a structure that is similar to the structure of the ankle joint prosthesis shown in Prahl U.S. Pat. No. 3,480,972, for example, there is a difference in structure that is significant in terms of the useful service life of the two prostheses. In the Prahl ankle joint prosthesis, and in similar prostheses, a tubular bushing of elastomer is disposed between and bonded to a rigid outer sleeve and an inner pin. The sleeve is attached to an artificial lower leg, for example, while the pin is attached to an artificial foot, for example. Flexion between the foot and the leg is accommodated by torsional deflection of the elastomeric bushing. The degree of the resulting strain in the elastomer of the bushing will depend upon the radial thickness of the bushing and the amount of rotational or torsional motion that must be accommodated. For a given amount of torsional motion, a relatively thin elastomeric bushing will experience relatively high strains and will provide a relatively short service life because of early fatigue failure of the elastomer. A thicker bushing will reduce the strains experienced by the elastomer and provide improved service life, but will also probably increase the overall size of the prosthesis. In addition, the effective spring rate of an element of elastomer at any distance from a point about which pivotal motion occurs is proportional to the spring rate of the elastomer in translational shear multiplied by the square of the distance from the pivot point. Since the elastomer that is closest to the pivot point is effectively much softer in rotational shear than elastomer that is farther from the pivot point, the major portion of the torsional strain or deflection in an elastomeric bushing, for example, will occur in the elastomer that is closest to the pivot point. Consequently, doubling the radial thickness of an elastomeric bushing will not halve the maximum strains experienced by the elastomer as it deflects to permit pivotal motion, but will have a much smaller effect on reducing the strains.

The prosthesis 10 affords a more efficient and effective method of controlling strains in its constituent mass of elastomer 68 because the rotational motion that is necessitated by flexion between the leg 12 and the foot 14 is accommodated by two distinct portions 70 and 72 of the elastomeric mass which are disposed at equal distances from the axis of pivotal motion. Approximately half of the rotational motion between the primary components 40 and 42 of the prosthesis 10 which is required by flexion between the foot 14 and the leg 12 is accommodated by deflection of the elastomer 70 between the pin 64 and the component 40. The other half of the motion is accommodated by deflection of the elastomer 72 between the pin 64 and the primary component 42 of the prosthesis 10. Thus, for the same diametral dimensions, the prosthesis 10 will effectively provide twice as much motion accommodation for a given maximum strain or half as much strain for a given degree of flexion as will a prosthesis constructed such as the one shown in the Prahl patent.

Figure 3:
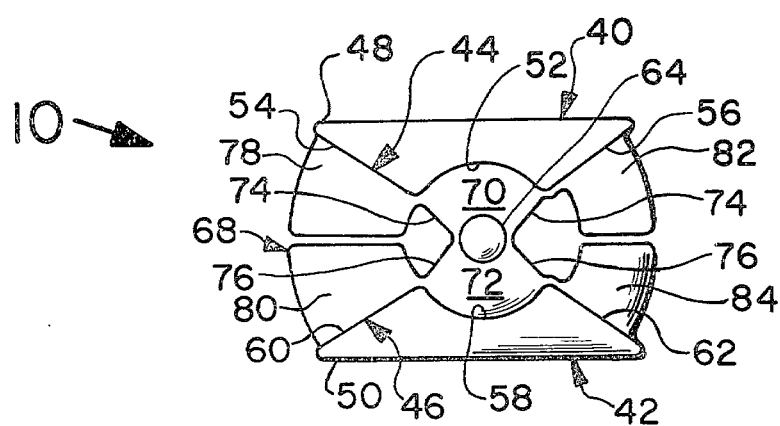
FIG. 3 is a side view, on an enlarged scale, of the ankle joint prosthesis of FIG. 1.

FIGS. 4 and 5 of the drawings illustrate another embodiment 10′ of the ankle joint prosthesis 10 shown in FIGS. 1, 2 and 3. In FIGS. 4 and 5, elements of the prosthesis 10′ that correspond to elements of the prosthesis 10 are designated with corresponding, but primed reference numerals. The prosthesis 10′, like the prosthesis 10, includes a pair of spaced apart, primary components 40′ and 42′ that are fabricated of a relatively non extensible material. Each of the primary components 40′ and 42′ includes a contoured surface 44′ or 46′ and an opposed planar surface 48′ or 50′. Disposed between concavely arcuate portions 52′ and 58′ of the contoured surfaces 44′ and 46′ is a cylindrical pin 64′ that is formed of a relatively inextensible material. Elastomeric elements 70′ and 72′ secure the pin 64′ to the components 40′ and 42′, respectively.

One difference between the prosthesis 10′ and the prosthesis 10 is that a single, one-piece rear bumper 86 is disposed between the components 40′ and 42′ of the prosthesis 10′, unlike the separate rear bumpers 78 and 80 of the prosthesis 10. The one-piece rear bumper 86 facilitates molding of the elastomeric portions of the prosthesis 10′ by eliminating the need to maintain a narrow space between two separate rear bumpers. In addition, the one-piece construction eliminates the possibility that dirt and grit will be introduced between two separate bumpers and thereafter abrade and wear the elastomer in the bumpers. The bumper 86 may, however, be subjected to tension loads during operation of the prosthesis 10′ to accommodate flexion. As previously discussed, tension loads are detrimental to the fatigue life of an elastomeric member, particularly when the tension loads alternate with compression loads, as would be the case with the bumper 86. Nonetheless, the bumper 86 will also be subjected to a compressive preload that results from the weight of the user of the prosthesis. The compressive preload will at least minimize, and perhaps totally eliminate, what would otherwise be tension loads on the bumper 86 as the prosthesis 10' flexes to bring the front portions of the primary components 40' and 42' of the prosthesis toward each other. The possibility of tension loads on the one-piece rear bumper 86 will also be reduced because the front portions 56' and 62' of the contoured surfaces 44' and 46', respectively, of the prosthesis components 40' and 42' are relatively close together, as compared to the corresponding surfaces 56 and 62 in the prosthesis 10. Thus, the plantar flexion of which the prosthesis 10' is capable is significantly less than the flexion of which the prosthesis 10 is capable.

Another difference between the prosthesis 10' and the prosthesis 10 is that the primary components 40' and 42' of the prosthesis 10' have roughly octagonal shapes in plan view, as shown in FIG. 5, as opposed to the rectangular shapes of the components 40 and 42 of the prosthesis 10. As should be apparent from FIG. 2, the octangonal shapes of the components 40' abd 42' eliminate the corners of the components 40 and 42 which project beyond the side surfaces or outline of the upper portion of the foot 14. The prosthesis 10' also includes relatively prominent grooves 88 formed in the surface of the rear bumper 86 adjacent the interfaces between the bumper and the primary components 40' and 42'. The grooves 88 tend to relieve the high stresses that might otherwise occur at the interfaces. The pin 64' includes a blind bore 90 in each end to facilitate locating the pin in its proper orientation and position in a mold for forming the elastomeric portions of the prosthesis 10'. Projections in the mold are provided to engage the blind bores 90 and hold the pin 64' in place during transfer and curing of the elastomer.

Yet another embodiment 10" of the present invention is illustrated in section in FIG. 8. As with the ankle joint prosthesis 10' of FIGS. 4 and 5, double primed reference numerals are used in FIG. 6 to designate elements of the prosthesis 10" that correspond to similarly referenced elements of the prosthesis 10. One difference between the ankle joint prosthesis 10" and the prosthesis 10 of FIGS. 1 and 2 is the incorporation into the prosthesis 10" of a one-piece rear bumper 92, similar to the one-piece rear bumper 86 of the prosthesis 10'. The rear bumper 92 is not formed wholly of elastomer, however, but includes a shim 94 formed of a relatively nonextensible material, such as metal or reinforced plastic. The shim 94 will theoretically reduce the ability of the elastomer in the bumper 92 to bulge under compressive loads. Consequently, as compared to a similar bumper without a shim, the bumper 92 should be able to support a substantially greater load for a given outward bulge or vertical deflection. The use of one or more shims 94 is a method of increasing the compression stiffness or spring rate of the rear bumper 92 without utilizing a type or grade of elastomer in the rear bumper that is different from the elastomer used elsewhere in the prosthesis. A problem with using the shim 94, however, is that there is a definite tendency for the shim to displace outwardly from the elastomer by moving to the left as viewed in FIG. 6, thereby defeating the intended purpose of the shim. A possible solution to the problem is to taper the shim 94 such that the thickest portion of the shim is closest to the pin 64.

The ankle joint prosthesis 10" of FIG. 6 incorporates a rotator 96 to supplement the capability of the basic prosthesis structure to accommodate internal and external rotation. The supplemental rotator 96 includes a cylindrical body of elastomeric material 98 in which are embedded three annular shims 100 that are fabricated of relatively nonextensible material. As with other components of the prostheses 10, 10' and 10", the elastomeric material 98 may be natural or synthetic rubber, while the inextensible material may be metal, reinforced plastic, or any other material which will bond to the elastomer 98 and which is relatively inextensible as compared to the elastomer. The rotator 96 is received in a recess 102 formed in the planar upper surface 48" of the primary component 40" of the prosthesis 10". Placing the rotator 96 in the recess 102 decreases the extent to which the rotator 96 increases the total height of the prosthesis 10". The elastomer 98 in the rotation 96 is bonded, at one end, to the surface 48" of the component 40" at the bottom of the recess 102 and, at the other end, to a supplemental plate 104. The plate 104 is spaced from the upper surface 48" of the primary prosthesis component 40" and is provided with two threaded bores 106. The bores 106 will accept screws (not shown) for securing the prosthesis 10" to an element such as a mounting adapter or an artificial lower leg. In operation, the rotator 96 will permit internal and external rotation of a foot through torsional shearing of the elastomer 98. The shims 100 will reduce the tendency of the rotator 96 to deflect under the weight of a user's body.

To guard against tension loads in the elastomer of both the rotator 96 and the rear bumper 92, a member 108 that is flexible, but relatively inextensible, such as a wire cable, extends between the lower primary component 42" of the prosthesis 10" and the supplemental plate 104 at the upper end of the prosthesis. The cable 108 is received in a bore 110 which is formed vertically through the center of the prosthesis 10" and which has a diameter sufficiently greater than the outer diameter of the cable to permit the prosthesis to function without interference from the cable. Buttons 112 at each end of the cable 108 hold the cable in place in the primary component 42" and the supplemental plate 104 of the prosthesis 10". The amount of compressive preload that is to be applied to the elastomeric elements of the prosthesis 10" will determine the amount of tension to be imposed on the cable 108. It would be possible to provide for adjustment of tension in the cable 108 during use of the prosthesis 10" by providing a threaded engagement between the buttons 112 and the cable, as suggested by Asbelle et al U.S. Pat. No. 3,982,280.

A fourth embodiment of an ankle joint prosthesis 10''' of the present invention is shown in FIGS. 7 and 8. As with the prostheses 10' and 10" of FIGS. 4 and 5 and FIG. 6, respectively, elements of the prosthesis 10''' of FIGS. 7 and 8 corresponding to elements of the prosthesis 10 of FIGS. 1 and 2 are designated with the same reference numerals as the elements of the prosthesis 10, but with a triple-prime superscript. Generally speaking, the ankle joint prosthesis 10''' closely resembles the ankle joint prosthesis 10' of FIGS. 4 and 5. There are two significant differences, one of which is the addition of curved shims 114 of nonextensible material to the portions 70''' and 72''' of the elastomeric mass 68''' which secure the pin 64''' to the primary components 40''' and 42''' of the prosthesis 10'''. The shims 114 will increase the compression load carrying capability of the prosthesis 10''' without significantly interfering with its ability to accommodate rotational motion of the components 40''' and 42''' of the prosthesis about the longitudinal axis of the pin 64''', for example. Another significant difference between the prosthesis 10''' and the prosthesis 10' is that the pin 64''' is arcuate in shape not only in planes normal to its longitudinal central axis 66''' but also in places that are parallel to and extend through the longitudinal axis of the pin, as best shown in FIG. 8. The arcuate portions 52''' and 58''' of contoured surfaces 44''' and 46''' of the primary components 40'''and 42''', respectively, are also curved in two perpendicular planes, as are the shims 114. The result of the double curvature of the outer surface of the pin 64''' and the corresponding surfaces of other elements in the prosthesis 10''' will be an increased ability of the prosthesis 10''' to accommodate inversion and eversion, as compared to the prostheses 10, 10' and 10''.

Although all of the foregoing embodiments of the invention have been ankle joint prostheses intended for use externally of the human body, the basic pivot structure that is incorporated in each of the foregoing embodiments of the invention may also be utilized in a joint prosthesis intended for use internally of the body. FIG. 9 of the drawings illustrates a finger joint prosthesis 116, for example, that incorporates two opposed and spaced apart primary components 118 and 120. The primary components 118 and 120 are formed of a relatively inextensible and physiologically inert material, such as titanium, stainless steel, cobalt-chromium alloys, nylon, silicone resins, or high density polyethylene. The components 118 and 120 include head portions 122 and 124, respectively, and shank or stem portions 126 and 128, respectively. The head portions 122 and 124 are each fixed to one end of their respective stem portions 126 and 128, which a relatively long and tapered to facilitate insertion into the intramedullary canals of the finger bones. The stem portions 126 and 128 of the components 118 and 120, respectively, will typically be cemented in place in their respective finger bones and may have specially contoured outer surfaces to improve the attachment to the bones. Alternatively, or additionally, the stem portions 126 and 128 may be coated with or formed from a porous material into which boney tissue may grow to secure the primary components 118 and 120 of the prosthesis 116 to their respective finger bones.

The head portions 122 and 124 of the primary components 118 and 120 of the prosthesis 116 include surfaces 130 and 132, respectively, that are arcuate in at least one plane. The concavely arcuate surfaces 130 and 132 of the head portions 122 and 124 are presented generally toward each other and are spaced apart from each other. Interposed between and spaced from each of the arcuate surfaces 130 and 132 is a cylindrical pin 134. The pin 134 is secured to the surface 130 by a body of resilient material 136 and to the surface 132 by a similar body of resilient material 138. Each of the bodies of resilient material 136 and 138 is preferably formed of an elastomer that is physiologically inert. When viewed in section taken normal to the central longitudinal axis 140 of the pin 134, each of the bodies of resilient material 136 and 138 resembles a truncated wedge. The curved base of each wedge-like body of resilient material 136 or 138 is bonded to a corresponding arcuate surface 130 or 132 of a component 118 or 120, while the curved, truncated apex of the resilient body 136 or 138 is bonded to the convexly arcuate outer surface of the pin 134. The bodies of resilient material 136 and 138 are bonded to the outer circumference of the pin 134 at approximately opposite locations and have pairs of exposed surfaces 142 and 144, respectively, that extend lengthwise of the pin 134 and outwardly from adjacent the circumference of the pin. The exposed surfaces 142 of the body of resilient material 136 are spaced apart from the exposed surfaces 144 of the body of resilient material 138 along all of their respective lengths measured in a generally radial direction outward from the pin 134.

In operation, the finger joint prosthesis 116 functions in much the same manner as the ankle joint prosthesis 10 of FIGS. 1 and 2. For example, flexion between adjacent bones in the finger into which the prosthesis 116 is implanted causes relative rotation between the pin 134 and one or both of the primary components 118 and 120 about an axis that is at least adjacent to and at least approximately parallel to the longitudinal axis 140 of the pin. The motion is resiliently permitted and accommodated through torsional deflection of the bodies of resilient material 136 and 138. The motion limiting effects provided by the front and rear bumpers 78, 80, 82, and 84 in the external ankle joint prosthesis 10 shown in FIGS. 1 and 2, for example, are provided for the prosthesis 116 by the muscles, tendons, and ligaments of the finger into which the prosthesis is implanted. The muscles and tendons will normally not be destroyed or rendered inoperative by the implantation procedure. Pivotal motions between the finger bones into which the prosthesis 116 is implanted which correspond to inversion and eversion and internal and external rotation of a foot will be accommodated primarily by compression and shearing, respectively, of the resilient bodies 136 and 138.

Although the bodies of resilient material 136 and 138 are illustrated as being wholly formed of elastomer, it would be possible to incorporate into the resilient bodies shims of nonextensible material, as was done in the ankle joint prosthesis 10''' of FIGS. 7 and 8. It is unlikely, however, that the compressive loads on the bodies of resilient material 136 and 138 in the finger joint prosthesis 116 will be of such a magnitude to require the addition of shims. Similarly, the pin 134, the bodies of resilient material 136 and 138, and the arcuate surfaces 130 and 132 of the prosthesis 116 might be curved both in planes that are normal to the longitudinal axis 140 of the pin and in planes that are parallel to the longitudinal axis and pass through the axis, as with the pin 64''' of FIG. 8. In a finger joint prosthesis for a proximal interphalangeal joint, the additional motion accommodation associated with such a double curvature is probably not required. On the other hand, in prostheses for other joints of the body, such as metacarpalphalangeal joints or shoulder joints, double curvature of the various components of the prostheses may be desirable to provide additional motion accommodation. The additional motion accommodation may also be afforded by shortening the length of the pin 134, for example, or by increasing the thicknesses of the bodies of resilient material 136 and 138, as measured generally radially of the pin 134. Conversely, lengthening the pin 134 or decreasing the thicknesses of the resilient bodies 136 and 138 will decrease the motion accommodation that is afforded about axes other than the axis 140 or an adjacent, parallel axis. Such structural adjustments to alter the motion accommodation characteristics of the prosthesis 116 may also be used in the prostheses 10, 10', 10'', and 10''' and in similar prostheses for replacement of other body joints. In this regard, although the illustrated embodiments of the invention are an ankle joint for external use and a finger joint for internal use, the prosthesis of the invention is suitable as an external or internal replacement for both an ankle joint and a finger joint and for other joints in the body, including shoulder joints, hip joints, elbow joints, and knee joints. In some joint prostheses, pivot members or pins that are curved in more than one plane may be a distinct advantage, if not a necessity.

As should be apparent from the various Figures of the drawings, the spacing between the two elastomeric sections that secure the pin to the primary components of each prosthesis may vary considerably. In the prosthesis 116 of FIG. 9, for example, the exposed surfaces 142 and 144 of the resilient bodies 136 and 138 are widely spaced apart, even at their closest points. In the prosthesis 10" of FIG. 6, on the other hand, the exposed surfaces 74" and 76" of the elastomeric sections 70" and 72", respectively, are relatively close together, particularly in the front of the prosthesis. It would be possible and acceptable, moreover, for the elastomeric sections 70" and 72", for example, to be completely interconnected and form a continuous annulus. The disadvantage of using a continuous annulus is that relative pivotal motion between the primary components of a prosthesis would require both torsional shearing and compression of the elastomer as soon as the motion began. Because any body of elastomer naturally has a compression modulus that is three or more times its shear modulus, the requirement for immediate compression loading would mean that pivotal motion would be more difficult to accommodate or, in other words, would require more actuating force.

It will be understood that the embodiments described above are merely exemplary and that persons skilled in the art may make many variations and modifications without departing from the spirit and scope of the invention. All such modifications and variations are intended to be within the scope of the invention as defined in the appended claims.

What is claimed is:

1. A joint prosthesis comprising:
   (a) a first relatively inextensible component;
   (b) a second relatively inextensible component that is spaced from the first component along a first axis;
   (c) means defining a relatively inextensible pivot member disposed between and spaced from each of the first and second components, the pivot member having a center and a central axis which passes through said center and which is oriented generally perpendicular to said first axis, the first and second components being disposed entirely on opposite sides of and separated by a plane oriented generally perpendicular to said first axis and generally parallel to said central axis of the pivot member; and
   (d) means for resiliently securing the pivot member to each of the first and second components, the securing means including (i) a first portion that secures the pivot member to the first component, and (ii) a second portion that secures the pivot member to the second component, each of the first and second portions of the securing means having at least one exposed surface that extends outwardly from adjacent the pivot member, said at least one exposed surface of the first portion of the securing means being spaced from said at least one exposed surface of the second portion of the securing means throughout at least a majority of their respective lengths measured generally radially of said central axis of the pivot member,
   the first and second components being coupled to each other only through the pivot member and the first and second portions of the securing means, the relative extensibility of the first and second components and the pivot member being determined in comparison to the securing means, the securing means resiliently permitting and accommodating relative rotation between the pivot member and the first component and between the pivot member and the second component so that the first and second components can move toward and away from each other in directions generally parallel to said first axis through rotation about a second axis that is disposed at least adjacent to and at least approximately parallel to the central axis of the pivot member.

2. A joint prosthesis, according to claim 1, wherein the pivot member is connected to each of the first and second components only through the securing means.

3. A joint prosthesis, according to claim 1, wherein the prosthesis is free of any substantially inextensible connection between the first and second components.

4. A joint prosthesis, according to claim 1, wherein at least one of the first and second components includes means for attaching said at least one component to a limb associated with a human body.

5. A joint prosthesis, according to claim 1, wherein the securing means is at least partially formed of elastomer.

6. A joint prosthesis, according to claim 5 wherein each of the first and second portions of the securing means is at least partially formed of elastomer.

7. A joint prosthesis, according to claim 6, wherein the first and second portions of the securing means are arcuately shaped when viewed in section taken generally normal to the central axis of the pivot member.

8. A joint prosthesis, according to claim 6, herein each of the first and second portions of the securing means has a pair of exposed surfaces, each exposed surface extending generally lengthwise of the pivot member and outwardly from adjacent the pivot member, the exposed surfaces of the first portion of the securing means being spaced from the exposed surfaces of the second portion of securing means throughout at least a majority of their respective lengths measured generally radially of the central axis of the pivot member.

9. A joint prosthesis, according to claim 1, wherein each of the first and second components includes a surface that is concavely arcuate in shape when viewed in section taken generally normal to the central axis of the pivot member, each of the arcuate surfaces of the first and second components being presented to and spaced from a convexly arcuate surface of the pivot member.

10. A joint prosthesis, according to claim 8, wherein each of the concavely arcuate surfaces of the first and second components is parallel to the convexly arcuate surface of the pivot member to which said each concavely arcuate surface is presented.

11. A joint prosthesis, according to claim 1, wherein the central axis of the pivot member is disposed between and spaced from each of the first and second components.

12. A joint prosthesis comprising:

(a) a first relatively inextensible component having a first arcuate surface;

(b) a second relatively inextensible component that is spaced from the first component along a first axis, the second component having a second arcuate surface spaced from the first arcuate surface;

(c) means defining a relatively inextensible pivot member that is diposed between and spaced from each of the first and second components, the pivot member having a center and a central axis which passes through said center and which is oriented generally perpendicular to said first axis, the first and second components being disposed entirely on opposite sides of and separated by a plane oriented generally perpendicular to said first axis and generally parallel to said central axis of the pivot member, the pivot member also having at least one arcuate surface and each of the first and second arcuate surfaces being presented to and spaced from an arcuate surface of the pivot member; and (d) means for resiliently securing the pivot member to each of the first and second components, the securing means including (i) a first portion which is at least partially formed of elastomer and which secures the pivot member to the first arcuate surface and (ii) a second portion which is at least partially formed of elastomer and which secures the pivot member to the second arcuate surface, each of the first and second portions of the securing means having at least one exposed surface that extends outwardly from adjacent the pivot member, said at least one exposed surface of the first portion of the securing means being spaced from said at least one exposed surface of the second portion of the securing means throughout at least a majority of their respective lengths measured generally radially of said central axis of the pivot member, the first and second components being coupled to each other only through the pivot member and the first and second portions of the securing means, the relative extensibility of the first and second components and the pivot member being determined in comparison to the elastomer of the securing means, the first and second portions of the securing means resiliently permitting and accommodating relative rotation between the pivot member and each of the first and second components so that the first and second components can move toward and away from each other in directions generally parallel to said first axis through rotation about a second axis that is disposed at least adjacent to and at least approximately parallel to the central axis of the pivot member.

13. A joint prosthesis, according to claim 12, wherein the pivot member is connected to the first and second components only through the first and second portions of the securing means.

14. A joint prosthesis, according to claim 12, wherein at least one of the first and second components includes means for attaching said at least one component to a limb associated with a human body.

15. A joint prosthesis, according to claim 12, wherein each of the first and second portions of the securing means has a pair of exposed surfaces, each exposed surface extending generally lengthwise of the pivot member and outwardly from adjacent the pivot member, the exposed surfaces of the first portion of the securing means being spaced from the exposed surfaces of the second portion of the securing means throughout at least a majority of their respective lengths measured generally radially of the central axis of the pivot member.

16. A joint prosthesis, according to claim 12, wherein each of the first and second surfaces is concavely arcuate and said at least one arcuate surface of the pivot member is convexly arcuate.

17. A joint prosthesis, according to claim 16, wherein each of the first and second arcuate surfaces is disposed parallel to an arcuate surface of the pivot member.

18. A joint prosthesis, according to claim 12, wherein said at least one arcuate surface of the pivot member and each of the first and second surfaces is arcuately shaped when viewed in section taken generally normal to the central axis of the pivot member.

19. A joint prosthesis, according to claim 12, wherein the pivot member is cylindrical in shape, and wherein the central axis of the pivot member is a central longitudinal axis of the pivot member.

20. A joint prosthesis, according to claim 12, wherein the central axis of the pivot member is disposed between and spaced from the first and second components.

21. An ankle joint prosthesis comprising:

(a) a first relatively inextensible component adapted to be connected with a leg member, said first relatively inextensible component having a front and a rear and a pair of opposed sides that extend between the front and the rear of the first component, the first component also having a first surface which is disposed between the opposed sides of the first component and between the front and the rear of the first component, at least a portion of the first surface extending from one side of the first component to the other side and having a concavely arcuate shape from front to rear;

(b) a second relatively inextensible component adapted to be connected with a foot member, said second relatively inextensible component having a front and a rear and a pair of opposed sides that extend between the front and the rear of the second component, the second component also having a second surface which is disposed between the opposed sides of the second component and between the front and the rear of the second component, at least a portion of the second surface extending from one side of the second component to the other side and having a concavely arcuate shape from front to rear, the second component being spaced from the first component and the second surface being presented generally toward the first surface;

(c) means defining a relatively inextensible pivot member that is disposed between and spaced from each of the first and second components, the pivot member being oriented to extend from side to side of each component and having at least one convexly arcuate surface, the arcuate portions of the first and second surfaces each being presented to and spaced from a convexly arcuate surface of the pivot member; and (d) means for resiliently securing the pivot member to each of the first and second components, the securing means including (i) a first portion which is at least partially formed of elastomer and which secures the pivot member to the arcuate portion of the first surface, (ii) a second portion which is at least partially formed of elastomer and which secures the pivot member to the arcuate portion of the second surface, and (iii) a third portion which is secured to at least one of the first and second components at a point behind the arcuate portion of the corresponding one of the first and second surfaces and which extends away from said at least one of the first and second components toward the other of said first and second components, the first and second portions of the securing means resiliently permitting and accommodating relative rotation between the pivot member and each of the first and second components so that the first and second components can rotate toward and away from each other about an axis that is disposed at least adjacent to and at least approximately parallel to a central axis of the pivot member, the first and second portions of the securing means including spaced apart segments disposed to rotate toward each other without exerting compressive forces on each other over a range of motion of said first and second components, the third portion of the securing means resiliently limiting relative rotational motion of the rear of the first component and the rear of the second component toward each other, the relative extensibility of the first and second components and the pivot member being determined in comparison to the elastomer of the securing means.

22. An ankle joint prosthesis, according to claim 21, wherein the third portion of the securing means is at least partially formed of elastomer.

23. An ankle joint prosthesis, according to claim 21, wherein the securing means also includes a fourth portion which is secured to at least one of the first and second components at a point in front of the arcuate portion of the corresponding one of the first and second surfaces and which extends away from said at least one of the first and second components to which said fourth portion is secured toward the other of the first and second components, the fourth portion of the securing means resiliently limiting relative rotational motion of the front of the first component and the front of the second component toward each other.

24. An ankle joint prosthesis, according to claim 23, wherein the fourth portion of the securing means is at least partially formed of elastomer.

25. An ankle joint prosthesis, according to claim 21, wherein the first and second components are coupled to each other only through the securing means and the pivot member.

26. An ankle joint prosthesis, according to claim 25, wherein the first and second components are coupled to each other only through the pivot member and the first and second portions of the securing means.

27. An ankle joint prosthesis, according to claim 21, wherein the pivot member is connected to the first and second components only through the first and second portions of the securing means.

28. An ankle joint prosthesis, according to claim 21, wherein the first component includes means for attaching said first component to an artificial leg, and wherein the second component includes means for attaching said second component to an artificial foot.

29. An ankle joint prosthesis, according to claim 21, wherein each of the concavely arcuate portions of the first and second surfaces is disposed parallel to a convexly arcuate surface of the pivot member.

30. An ankle joint prosthesis, according to claim 21, wherein the pivot member is cylindrical in shape, and wherein the central axis of the pivot member is a central longitudinal axis of the pivot member.

31. An ankle joint prosthesis, according to claim 21, wherein the central axis of the pivot member is disposed between and spaced from both the first and second components.

32. An ankle joint prosthesis comprising:
 (a) a first relatively inextensible component having a front and a rear and a pair of opposed sides that extend between the front and the rear of the first component, the first component also having a first surface which is disposed between the opposed sides of the first component and between the front and the rear of the first component, at least a portion of the first surface extending from one side of the first component to the other side and having a concavely arcuate shape from front to rear;
 (b) a second relatively inextensible component having a front and a rear and a pair of opposed sides that extend between the front and the rear of the second component, the second component also having a second surface which is disposed between the opposed sides of the second component and between the front and the rear of the second component, at least a portion of the second surface extending from one side of the second component to the other side and having a concavely arcuate shape from front to rear, the second component being spaced from the first component and the second surface being presented generally toward the first surface;
 (c) means defining a relatively inextensible pivot member that is disposed between and spaced from each of the first and second components, the pivot member being oriented to extend from side to side of each component and having at least one convexly arcuate surface, the arcuate portions of the first and second surfaces each being presented to and spaced from a convexly arcuate surface of the pivot member; and
 (d) means for resiliently securing the pivot member to each of the first and second components, the securing means including (i) a first portion which is at least partially formed of elastomer and which secures the pivot member to the arcuate portion of the first surface, (ii) a second portion which is at least partially formed of elastomer and which secures the pivot member to the arcuate portion of the second surface, each of said first and second portions of the securing means having a pair of exposed surfaces, each exposed surface extending generally lengthwise of said pivot member and generally outwardly from said pivot member, the exposed surfaces of said first portion being spaced from the exposed surfaces of said second portion throughout a majority of their respective lengths measured generally radially outwardly of the pivot member, and (iii) a third portion which is secured to at least one of the first and second components at a point behind the arcuate portion of the corresponding one of the first and second surfaces and which extends away from said at least one of the first and second components toward the other of said first and second components, the first and second portions of the securing means resiliently pemitting and accommodating relative rotation between the pivot member and each of the first and second components so that the first and second components can rotate toward and away from each other about an axis that is disposed at least adjacent to and at least approximately parallel to a central axis of the pivot member, the third portion of the securing means resiliently limiting relative rotational motion of the rear of the first component and the rear of the second component toward each other, the relative extensibility of the first and second components and the pivot member being determined in comparison to the elastomer of the securing means.

33. An ankle joint prosthesis comprising:
(a) a first relatively inextensible component having a front and a rear and a pair of opposed sides that extend between the front and the rear of the first component, the first component also having a first surface which is disposed between the opposed sides of the first component and between the front and the rear of the first component, at least a portion of the first surface extending from one side of the first component to the other side and having a concavely arcuate shape from front to rear, a portion disposed in front of the arcuate portion and a portion disposed to the rear of the arcuate portion;
(b) a second relatively inextensible component having a front and a rear and a pair of opposed sides that extend between the front and the rear of the second component, the second component also having a second surface which is disposed between the opposed sides of the second component and between the front and the rear of the second component, at least a portion of the second surface extending from one side of the second component to the other side and having a concavely arcuate shape from front to rear, a portion disposed in front of the arcuate portion and a portion disposed to the rear of the arcuate portion, the second component being spaced from the first component and the second surface being presented generally toward the first surface with the front portions of the first and second surfaces being disposed to diverge from each other from rear to front, and the rear portions of the first and second surfaces being disposed to diverge from the front to rear;
(c) means defining a relatively inextensible pivot member that is disposed between a spaced from each of the first and second components, the pivot member being oriented to extend from side to side of each component and having at least one convexly arcuate surface, the arcuate portions of the first and second surfaces each being presented to and spaced from a convexly arcuate surface of the pivot member; and
(d) means for resiliently securing the pivot member to each of the first and second components, the securing means including (i) a first portion which is at least partially formed of elastomer and which secures the pivot member to the arcuate portion of the first surface, (ii) a second portion which is at least partially formed of elastomer and which secures the pivot member to the arcuate portion of the second surface, and (iii) a third portion which is secured to at least one of the first and second components at a point behind the arcuate portion of the corresponding one of the first and second surfaces and which extends away from said at least one of the first and second components toward the other of said first and second components, the first and second portions of the securing means resiliently pemitting and accommodating relative rotation between the pivot member and each of the first and second components so that the first and second components can rotate toward and away from each other about an axis that is disposed at least adjacent to and at least approximately parallel to a central axis of the pivot member, the third portion of the securing means resiliently limiting relative rotational motion of the rear of the first component and the rear of the second component toward each other, the relative extensibility of the first and second components and the pivot member being determined in comparison to the elastomer of the securing means.

34. An ankle joint prosthesis, according to claim 33, wherein the third portion of the securing means is secured to the rear portion of at least one of the first and second surfaces and extends toward the rear portion of the other of the first and second surfaces.

35. An ankle joint prosthesis comprising:
(a) a first relatively inextensible component having a front and a rear and a pair of opposed sides that extend between the front and the rear of the first component, the first component also having a first surface which is disposed between the opposed sides of the first component and between the front and the rear of the first component, at least a portion of the first surface extending from one side of the first component to the other side and having a concavely arcuate shape from front to rear;
(b) a second relatively inextensible component having a front and a rear and a pair of opposed sides that extend between the front and the rear of the second component, the second component also having a second surface which is disposed between the opposed sides of the second component and between the front and the rear of the second component, at least a portion of the second surface extending from one side of the second component to the other side and having a concavely arcuate shape from front to rear, the second component being spaced from the first component and the second surface being presented generally toward the first surface;
(c) means defining a relatively inextensible pivot member that is disposed between and spaced from each of the first and second components, the pivot member being oriented to extend from side to side of each component and having at least one convexly arcuate surface, the arcuate portions of the first and second surfaces each being presented to and spaced from a convexly arcuate surface of the pivot member;
(d) means for resiliently securing the pivot member to each of the first and second components, the securing means including (i) a first portion which is at least partially formed of elastomer and which secures the pivot member to the arcuate portion of the first surface, (ii) a second portion which is at least partially formed of elastomer and which secures the pivot member to the arcuate portion of the second surface, and (iii) a third portion which is secured to at least one of the first and second components at a point behind the arcuate portion of the corresponding one of the first and second surfaces and which extends away from said at least one of the first and second components toward the other of said first and second components, the first and second portions of the securing means resiliently pemitting and accommodating relative rotation between the pivot member and each of the first and second components so that the first and second components can rotate toward and away from each other about an axis that is disposed at least adjacent to and at least approximately parallel to a central axis of the pivot member, the third portion of the securing means resiliently limiting relative rotational motion of the rear of the first component and the rear of the second component toward each other, the relative extensibility of the first and second components and the pivot member being determined in comparison to the elastomer of the securing means;

(e) a relatively inextensible plate member spaced from the first component and disposed adjacent a surface of the first component opposite both the first surface and the second component; and (f) a body of resilient material disposed between and secured to the plate member and the first component, the resilient body permitting the accommodating relative rotation between the plate member and the first component.

36. An ankle joint prosthesis, according to claim 35, wherein the rotator means also includes at least one shim of substantially inextensible material embedded in the body of resilient material and spaced from both the plate member and the first component.

37. A prosthesis for replacing a skeletal joint in a human body comprising a first joint component adapted for connection with a first element, a second joint component adapted for connection with a second element, at least one of said first and second elements being a portion of a human body, a pivot component disposed between said first and second joint components, means for resiliently connecting said pivot component to said first and second joint components, said resilient means including a first body of elastomeric material disposed between and attached to said first joint component and said pivot component, a second body of elastomeric material disposed between and attached to said second joint component and said pivot component, said first and second bodies of elastomeric material being spaced apart and suspending said pivot component between said first and second joint components to permit motion of said first and second joint components relative to each other about said pivot component in simulating the operation of a skeletal joint in a human body.

38. A prosthesis as defined in claim 37 wherein said first body of elastomeric material includes a first side surface and said second body of elastomeric material includes a second side surface, said first and second bodies of elastomeric material being deflectable to allow said first and second joint components to move toward each other and relative to said pivot component, said first and second side surfaces on said bodies of elastomeric material being disposed on opposite sides of a plane which extends through said pivot component, said first and second side surfaces being further disposed to move toward each other and toward said plane over a range of movement of said first and second joint components toward each other.

39. A prosthesis as defined in claim 38 wherein said pivot component comprises a pin having at least one arcuate outer surface circumscribing a longitudinal central axis, said first and second bodies of elastomeric material being deflectable about axes which are parallel to the central axis of said pin to allow said first and second joint components to rotate toward and away from each other about the outer surface of said pin, said first and second side surfaces of said first and second bodies of elastomeric material extending generally away from the outer surface of said pin, said first and second side surfaces being disposed on opposite sides of a plane which intersects said pin and is oriented parallel to the central axis of said pin, said first and second side surfaces being further disposed to move toward each other and toward said plane as said first and second joint components move toward each other about said pin.

* * * * *